United States Patent
Hu et al.

(10) Patent No.: US 8,546,644 B2
(45) Date of Patent: Oct. 1, 2013

(54) RECOMBINANT GENE WHICH ENHANCES THE ABILITY OF FISH TO TOLERATE LOW DISSOLVED OXYGEN STRESS AND THE USE THEREOF

(75) Inventors: Wei Hu, Beijing (CN); Zuoyan Zhu, Beijing (CN); Hong Ma, Beijing (CN); Bo Guan, Beijing (CN); Yuanlei Hu, Beijing (CN); Zhongping Lin, Beijing (CN)

(73) Assignees: Institute of Hydrobiology, Chinese Academy of Sciences, Wuhan (CN); Peking University, Beijing (CN)

( * ) Notice: Subject to any disclaimer, the term of this patent is extended or adjusted under 35 U.S.C. 154(b) by 385 days.

(21) Appl. No.: 12/879,931

(22) Filed: Sep. 10, 2010

(65) Prior Publication Data

US 2011/0099648 A1 Apr. 28, 2011

(30) Foreign Application Priority Data

Oct. 27, 2009 (CN) .......................... 2009 1 0272539

(51) Int. Cl.
*A01K 67/027* (2006.01)
*C12N 15/85* (2006.01)
*C12N 15/873* (2010.01)
*C12N 15/90* (2006.01)

(52) U.S. Cl.
USPC .............................. 800/20; 800/25; 435/320.1

(58) Field of Classification Search
USPC .................................. 800/20, 25; 435/320.1
See application file for complete search history.

(56) References Cited

PUBLICATIONS

Yan et al. (2000) Cell Res., vol. 10, 17-27.*
Fu et al. (2005) Rev. Sci. Tech. Off. Int. Epiz., vol. 24(1), 299-307.*
Giles, M.A. 1991 "Strain differences in hemoglobin polymorphism, oxygen consumption, and blood oxygen equilibria in three hatchery broodstocks of Arctic charr, *Salvelinus alpinus*" *Fish Physiology and Biochemistry* 9(4):291-301.
Hoppeler, H. et al. 2001 "Muscle tissue adaptations to hypoxia" *Journal of Experimental Biology* 204:3133-3139.
Nitta, T. et al. 2003 "Myoglobin Gene Expression Attenuates Hepatic Ischemia Reperfusion Injury" *Journal of Surgical Research* 110:322-331.
Pesce, A. et al. 2002 "Neuroglobin and cytoglobin Fresh blood for the vertebrate globin family" *EMBO Reports* 3(12):1146-1151.
Orii, Y. et al. "Photodissociation of Oxygenated Cytochrome o(s) (*Vitreoscilla*) and Kinetic Studies of Reassociation" *Journal of Biological Chemistry* 261(8):3544-3547, 1986.
Sambrook, J. et al. 2000 *Molecular Cloning: A Laboratory Manual* 3rd Ed., Cold Spring Harbor Laboratory Press, Chapters 1-18. (uploaded via EFS Web as Part 1: 200 pages, and Part 2: 172 pages).
Skjæraasen, J.E. et al. 2008 "Hypoxic avoidance behaviour in cod (*Gadus morhua* L.): The effect of temperature and haemoglobin genotype" *Journal of Experimental Marine Biology and Ecology* 358:70-77.
Terwilliger, N.B. 1998 "Functional Adaptations of Oxygen-Transport Proteins" *Journal of Experimental Biology* 201:1085-1098.
Vogt, M. et al. 2001 "Molecular adaptations in human skeletal muscle to endurance training under simulated hypoxic conditions" *J. Appl. Physiol* 91:173-182.
Wakabayashi, S. et al. 1986 "Primary sequence of a dimeric bacterial haemoglobin from *Vitreoscilla*" *Nature* 322:481-483.
Westerfield, M. 2007 "General Methods for Zebrafish Care and Breeding" in *The Zebrafish Book: A guide for the Laboratory use of zebrafish* (*Danio rerio*), 5th Edition, Eugene, University of Oregon. Press, pp. 1-36.
Zhu, Z. et al. 1985 "Novel gene transfer into the fertilized eggs of gold fish (*Carassius auratus* L. 1758)" *Institute of Hydrobiology*, Academia Sinica pp. 31-34.

* cited by examiner

*Primary Examiner* — Anne Marie S Wehbe
(74) *Attorney, Agent, or Firm* — Knobbe, Martens, Olson & Bear, LLP

(57) ABSTRACT

The invention discloses a recombinant gene which enhances the ability of fish to tolerate low dissolved oxygen (DO) stress and the use thereof. Carp β-actin gene promoter is used as a promoter and *Vitreoscilla* hemoglobin gene is used as a target gene, so as to construct the recombinant *Vitreoscilla* hemoglobin gene driven by carp β-actin promoter. The modeling organism zebrafish is used as the research object, and the recombinant gene is microinjected into zygotes of zebrafish. After PCR screening and 156 h low DO stress test, transgenic fish are obtained with a survival rate of 92%, which is significantly different from the survival rate of 65% of the control fish group. The vhb transgenic zebrafish obtain hypoxia tolerance. When the recombinant gene is applied to the economically farmed species, i.e., blunt snout bream (*Megalobrama amblycephala*) and common carp (*Cyprinus carpio* L.), it enhances their hypoxia tolerance as well. Such genetically improved breeding technique may be widely used for breeding new excellent farmed species with the hypoxia tolerance.

9 Claims, 3 Drawing Sheets

RECOMBINANT GENE WHICH ENHANCES THE ABILITY OF FISH TO TOLERATE LOW DISSOLVED OXYGEN STRESS AND THE USE THEREOF

CROSS-REFERENCE TO RELATED APPLICATIONS

This application claims the benefit of Chinese application No. 200910272539.1, filed Oct. 27, 2009.

BACKGROUND OF THE INVENTION

1. Field of the Invention

The invention relates to the field of genetic breeding for aquatic animals, in particularly to a recombinant gene which enhances the hypoxia tolerance. The invention also relates to the use of such recombinant gene for genetically improving farmed species.

2. Description of the Related Art

Dissolved oxygen (DO) is the most important environmental factor in aquiculture, which may be affected by temperature, diurnal rhythm, seasonal variation and eutrophication, etc. Fish are very sensitive to the variation of DO condition in the water. Low DO reduces the growth rate of fish, induces endocrine disorders of fish, impacts metabolism and reproduction features of fish, changes the behavior and distribution of fish, and even results in the death of fish. Therefore, the abundance, diversity and capture amount of fish are all severely impaired in the water areas affected by low DO. As a result, it is practically worth to develop novel farmed species with the hypoxia tolerance using transgenic technology.

Currently, the study of improving hypoxia tolerance in fish using transgenic technology is still a presumption. The hypoxia tolerance in fish mainly relies on the contents and types of globulin families and oxygen affinity (Giles M. A (1991). Strain differences in hemoglobin polymorphism, oxygen consumption, and blood oxygen equilibria in three hatchery broodstocks of Arctic charr, *Salvelinus alpinus*. *Fish Physiology and Biochemistry* 9: 291-301. 2, Terwilliger N. B (1998). Functional adaptations of oxygen-transport proteins. *J. Exp. Biol.* 201(8): 1085-1098. 3, Skjæaasen J. E., Nilsen T., Meager J. J., Herbert N. A., Moberg O., Tronci V., Johansen T., Salvanes A. G. V (2008). Hypoxic avoidance behaviour in cod (*Gadus morhua* L.): The effect of temperature and haemoglobin genotype. Journal of Experimental Marine Biology and Ecology; 358; 70-77.). Four types of globulins were found in human and other vertebrates: haemoglobin (Hb), myoglobin (Mb), neuroglobin and cytoglobin. These four types of globulins vary to some extent in structure, tissue distribution and function (4, Pesce A., Bolognesi M., Bocedi A., Ascenzi P., Dewilde S., Moens L., Hankeln T., Burmester T. (2002). Neuroglobin and cytoglobin. Fresh blood for the vertebrate globin family. *EMBO Rep.* 3(12):1146-1151.). In mammals, haemoglobin (Hb) and myoglobin (Mb) may be induced by low oxygen and hypoxia (5, Hoppeler H., Vogt M. (2001). Muscle tissue adaptations to hypoxia. J. Exp. Biol. 204: 3133-3139. 6, Vogt M., Puntschart A., Geiser J., Zuleger C., Billeter R., and Hoppeler H. (2001). Molecular adaptations in human skeletal muscle to endurance training under simulated hypoxic conditions. *J. Appl. Physiol.* 91: 173-182. 7, Nitta T., Xundi X., Hatano E., Yamamoto N., Uehara T., Yoshida M., Harada N., Honda K., Tanaka A. & Sosnowski D. (2003). Myoglobin gene expression attenuates hepatic ischemia reperfusion injury. *J. Surg. Res.* 110: 322-331.).

Strictly speaking, *Vitreoscilla stercoraria* is an aerobe, but they are able to adapt to hypoxia by expressing soluble haemoglobin (*Vitreoscilla* hemoglobin, VHb) which consists of 2 identical subunits of 15,775 Da and 2 heme molecules (Wakabayashi S., Matsubara H., Webster D. A. (1986). Primary sequence of a dimeric bacterial hemoglobin from *Vitreoscilla*. *Nature* 322:481-483.). Although VHb does not increase intracellular oxygen concentration, it can accelerate oxygen delivery in a low oxygen condition due to the high dissociation rate constant between VHb and oxygen molecules, and thus improves respiration and energy metabolism. Therefore, hypoxia tolerance in fish may be prospectively enhanced by introducing VHb gene into fish, so as to develop novel farmed species with hypoxia tolerance.

Zebrafish (*Danio rerio*) is a fish model currently widely used in many investigations such as Developmental Biology and Hydrobiont Technology (Westerfield M. (1993). The Zebrafish Book: A Guide for the Laboratory Use of Zebrafish (*Brachydanio rerio*). University of Oregon Press, Eugene, Oreg.). A new method, where zebrafish is used as a model to study the improvement of the ability of recipient fish to tolerate low oxygen stress, results in an instructive significance for breeding novel economically farmed species with tolerance to low DO stress. Based on breeding of the transgenic zebrafish with the hypoxia tolerance, the recombination technique is further applied to other important economically farmed species such as blunt snout bream (*Megalobrama amblycephala*) and common carp (*Cyprinus carpio* L.). The resultant vhb transgenic blunt snout bream and common carp also have the hypoxia tolerance.

SUMMARY OF THE INVENTION

The purpose of the invention is to provide a recombinant gene which enhances the hypoxia tolerance in fish (the recombinant gene of *Vitreoscilla* hemoglobin (VHb) driven by carp β-actin gene promoter). *Vitreoscilla* hemoglobin consists of 2 identical subunits of 15,775 Da and 2 heme molecules (Wakabayashi S., Matsubara H., Webster D. A. (1986). Primary sequence of a dimeric bacterial hemoglobin from *Vitreoscilla*. *Nature* 322:481-483.). Due to the high dissociation rate constant between VHb and oxygen molecules and the strong regulatory ability of the β-actin gene promoter, the recombinant gene can ensure the acceleration of oxygen delivery and the enhancement of respiration and energy metabolism in the recipient animals under hypoxia.

Another purpose of the invention is to provide a use of the recombinant gene which enhances hypoxia tolerance in fish. The recombinant vhb gene driven by carp β-actin gene promoter is microinjected into zygotes of zebrafish. Then the 7-day transgenic fish obtained by screening are subjected to low oxygen stress treatment in a low DO (0.91 mg/l) stress condition for 156 h. The survival rate of these transgenic fish is 92%, which is significantly different from the survival rate of 65% of the control sister fish group. The introduction of the recombinant gene enhances the hypoxia tolerance and provides a commonly applicable method for breeding novel economically farmed species with hypoxia tolerance. The transgenic blunt snout bream and transgenic common carp bred by same method have the feature of hypoxia tolerance.

A further purpose of the invention is to provide a fish species with enhanced hypoxia tolerance, wherein said fish comprises the above recombinant *Vitreoscilla* hemoglobin (VHb) driven by carp β-actin gene promoter. In one embodiment, said fish comprises a vector with a sequence shown as SEQ ID NO: 5. In another embodiment, said fish is an economically farmed species. In a further embodiment, said fish is zebrafish, blunt snout bream or common carp.

To achieve the above purposes, the following technical approaches are used in the invention.

Carp actin gene promoter (cloned from the genomic bank of carps, a conventional protocol, Molecular Cloning A Laboratory Mannual, 2$^{nd}$ ed., Sambrook, J. et al. Science Press, 1993) is used as a promoter; and *Vitreoscilla* hemoglobin (VHb) is used as a target gene (VHb is cloned from *Vitreoscilla stercoraria* commercially purchased from ATCC center, USA, with the ATCC number 15128). The 5' upstream primer is CCATGGTAGA CCAGCAACC (SEQ ID NO: 6), and the 3' downstream primer is GGGTAACCTT TATTCAACCG (SEQ ID NO: 7). PCR condition is shown as follows: pre-denaturalizing at 94° C. for 10 min; 25 cycles of denaturalizing at 94° C. for 30 sec, annealing at 52° C. for 45 sec, extending at 72° C. for 45 sec; then 72° C. for 7 min. A 441 bp fragment is amplified and recovered, and then cloned into a pGEM-T-easy vector (Tiangen Co.), so as to construct an expression vector of *Vitreoscilla* hemoglobin (VHb) gene driven by carp β-actin gene promoter (a conventional protocol, Molecular Cloning A Laboratory Mannual, 2$^{nd}$ ed., Sambrook, J. et al. Science Press, 1993) and thus develop transgenic fish with the hypoxia tolerance.

The invention includes the following steps:

1. Recombinant Gene and the Preparation Method Thereof

The recombinant *Vitreoscilla* hemoglobin (VHb) gene driven by the carp β-actin gene promoter is constructed. The detailed steps are shown as follows.

(1) Carp actin gene promoter is used as a promoter (cloned from the genomic bank of carps, a conventional protocol, Molecular Cloning A Laboratory Mannual, 2$^{nd}$ ed., Sambrook, J. et al. Science Press, 1993; its nucleotide sequence is shown as SEQ ID No. 1, see Sequence Listing); and *Vitreoscilla* hemoglobin gene is used as a target gene, which is cloned from *Vitreoscilla stercoraria* commercially purchased from ATCC center, USA, with the ATCC number 15128. The 5' upstream primer is CCATGGTAGA CCAGCAACC (SEQ ID NO: 6), and the 3' downstream primer is GGGTAACCTT TATTCAACCG (SEQ ID NO: 7). PCR condition is shown as follows: pre-denaturalizing at 94° C. for 10 min; 25 cycles of denaturalizing at 94° C. for 30 sec, annealing at 52° C. for 45 sec° C. extending at 72° C. for 45 sec; then 72° C. for 7 min. A 441 bp fragment with a nucleotide sequence shown as SEQ ID No. 2 (see Sequence Listing) is amplified and recovered, and then cloned into a pGEM-T-easy vector (Tiangen Co.). Simian virus 40 poly A (Clontech Co.) is used as a terminating sequence, the nucleotide sequence of which is shown as SEQ ID No. 3 (see Sequence Listing).

(2) The enhanced green fluorescent protein eGFP (Clontech Co.) driven by cytomegalovirus CMV (Clontech Co.) promoter is used as a reporter gene, the nucleotide sequence of which is shown as SEQ ID No. 4 (see Sequence Listing).

(3) After digested by restriction enzymes (XhoI, SmaI, Not I and Hind III), the above four gene fragments (SEQ ID NO: 1, SEQ ID NO: 2, SEQ ID NO: 3, SEQ ID NO: 4) are ligated with plasmid vector PUC118 (SABC Co.) (a conventional protocol, Molecular Cloning A Laboratory Mannual, 2$^{nd}$ ed., Sambrook, J. et al. Science Press, 1993). An expression vector containing the recombinant gene is obtained and named as pCVCG, the nucleotide sequence of which is shown as SEQ ID NO: 5. In such recombinant gene, *Vitreoscilla* hemoglobin consists of 2 identical subunits of 15,775 Da and 2 heme molecules (Wakabayashi S., Matsubara H., Webster D. A. (1986). Primary sequence of a dimeric bacterial hemoglobin from *Vitreoscilla. Nature* 322:481-483.). The association rate constant ($k_{on}$ 78 µM$^{-1}$ s$^{-1}$) between *Vitreoscilla* hemoglobin and oxygen molecules is similar to that for other hemoglobins; whereas the dissociation rate constant ($k_{off}$ 5000 s$^{-1}$) between *Vitreoscilla* hemoglobin and oxygen molecules is higher than that for other hemoglobins by hundreds of folds (Orii Y., Webster D. A. Photodissociation of oxygenated cytochrome o(s) (*Vitreoscilla*) and kinetic studies of reassociation. J Biol Chem 1986; 261:3544-3547.). Therefore, oxygen delivery may be accelerated in a low oxygen condition, and thus respiration and energy metabolism may be improved.

2. The Use of a Recombinant Gene Enhancing the Ability of Fish to Tolerate Low do Stress for Genetically Improved Farmed Species, Comprising the Following Steps:

(1) Preparation of Transgenic Fish

The expression vector pCVCG containing the recombinant gene is microinjected into zygotes of fish (Zhu Z, Li G, He L, et al. Novel gene transfer into the fertilized eggs of goldfish (*Carassius auratus* L. 1758). Z angew Ichthyol, 1985, 1:31-34).

(2) Screening of the Transgenic Fish with the Hypoxia Tolerance

The green fluorescent protein expression is observed under a fluorescent dissecting microscope (Olympus Model SZX12). The recombinant gene is tested by PCR and the transgenic fish with the hypoxia tolerance is obtained by a low DO screening experiment.

The invention has the following advantages and effects. The invention provides a genetically improved new breeding technique for enhancing the ability of fish to tolerate low DO stress. The 7-day transgenic zebrafish bred with such method is subject to low oxygen stress treatment in a low DO (0.91 mg/l) stress condition for 156 h. The survival rate of those transgenic fish is 92%, which is significantly different from survival rate of 65% of the control sister fish group. The transgenic blunt snout bream and transgenic carps bred by such method both have the hypoxia tolerance. This genetically improved breeding technique may be widely used for breeding new excellent farmed species with the hypoxia tolerance.

DETAILED DESCRIPTION OF THE PREFERRED EMBODIMENT

Example 1

Construction of pCVCG, The Expression Vector Containing *Vitreoscilla* Hemoglobin Gene In the expression vector of *Vitreoscilla* hemoglobin gene, carp actin gene promoter with a length of 1213 bp was used as a promoter (SEQ ID NO: 1, which was screened from the genomic bank of carps, a conventional protocol, Molecular Cloning A Laboratory Mannual, $2^{nd}$ ed., Sambrook, J. et al. Science Press, 1993). *Vitreoscilla* hemoglobin gene with a length of 441 bp, as a target gene (SEQ ID NO: 2, which was cloned from *Vitreoscilla* stercoraria commercially purchased from ATCC Center, USA, with the ATCC number 15128. The 5' upstream primer was CCATGGTAGA CCAGCAACC (SEQ ID NO: 6), and the 3' downstream primer was GGG-TAACCTT TATTCAACCG (SEQ ID NO: 7). PCR condition was shown as follows: pre-denaturalizing at 94° C. for 10 min; 25 cycles of denaturalizing at 94° C. for 30 sec, annealing at 52° C. for 45 sec, extending at 72° C. for 45 sec; then 72° C. for 7 min. The amplified fragments with a length of 441 bp were recovered, and then cloned into a pGEM-T-easy vector) was inserted downstream of the promoter, followed by simian virus 40 poly A (Clontech Co.) as a terminating sequence and CMV promoter (Clontech Co.) driven enhanced green fluorescent protein eGFP (Clontech Co.) as a reporter gene. The vector frame was PUC118 (SABC Co.).
1) The detailed construction process is shown as follows.

The carp actin gene promoter was completely digested by XhoI and SmaI; *Vitreoscilla* hemoglobin gene was completely digested by SmaI and Not I; simian virus 40 poly A was completely digested by Not I and Hind III; CMV promoter-driven enhanced green fluorescent protein eGFP gene was completely digested by Hind III and XbaI; and PUC118 plasmid was completely digested by XhoI and XbaI. The resultant fragments were ligated with T4 ligase at 16° C. for 4 hours, respectively. The restriction enzymes and ligase used above were all purchased from Takara Co.

*E. coli* (*E. coli* TOP10, purchased from Invitrogen, with a genotype of F-mcrAΔ(mrr-hsdRMS-mcrBC) Φ80lacZΔM15ΔlacX74 deoR recA1 araD139α(ara-leu)7697 galU galK rpsL (StrR) endA1 nupG) was transformed by the above ligation solution; cultured at a constant temperature of 37° C.; and inoculated and cultured in LB broth for further identification.

Figure 1:
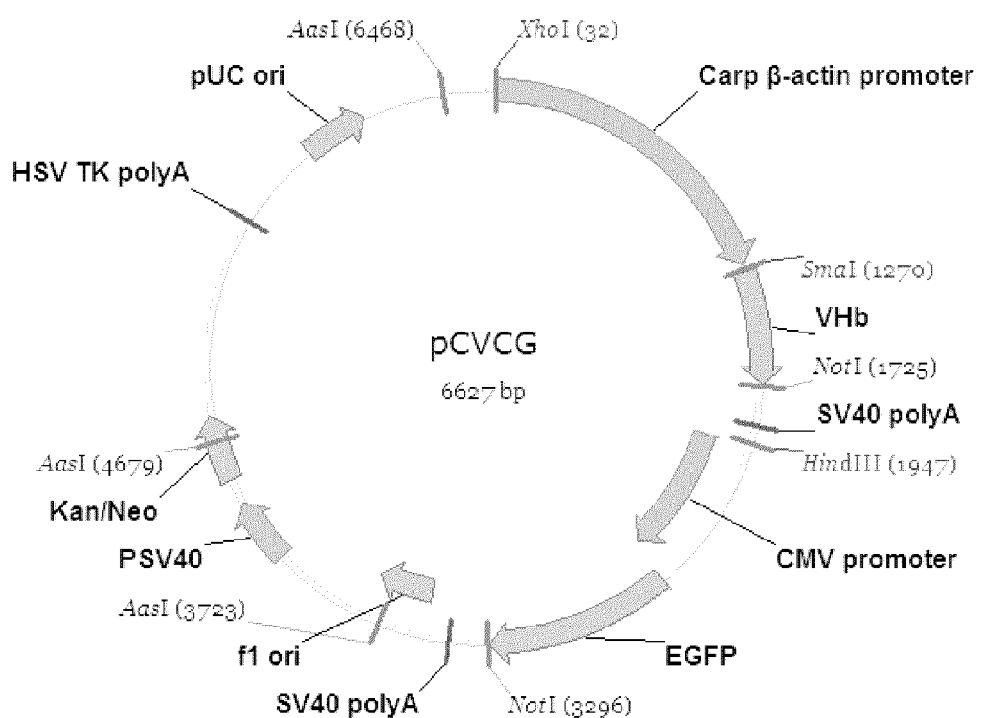
FIG. 1 is a diagram showing pCVCG, the expression vector of *Vitreoscilla* hemoglobin gene, wherein carp actin gene promoter is 1213 bp in length; *Vitreoscilla* hemoglobin gene is 441 bp in length; simian virus 40 poly A is 51 bp in length; and CMV promoter-driven eGFP is 1331 bp in length.
Figure 2:
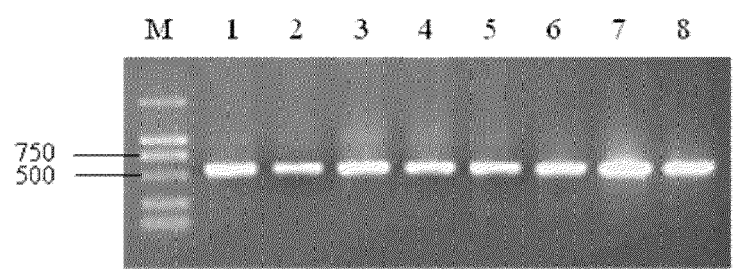
FIG. 2 shows the positive screening of pCVCG, the expression vector of *Vitreoscilla* hemoglobin gene, wherein M: DNA Marker DL2000; 1-8: pCVCG positive clones.
Figure 3:
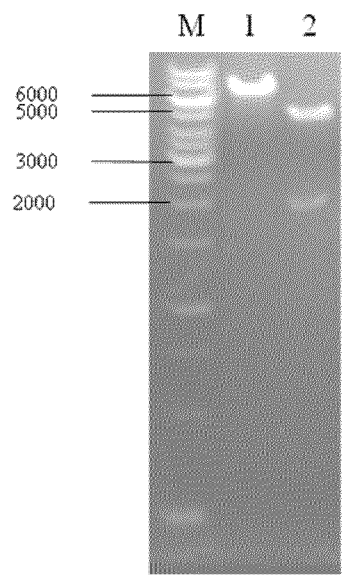
FIG. 3 is an electrophoretic image of the digested pCVCG, the expression vector of *Vitreoscilla* hemoglobin gene, wherein M: GeneRuler™ 1 kb DNA Ladder; 1: HindIII single digestion; 2: XhoI+HindIII double digestion.

The above PCR, digestion, ligation, DNA transformation, bacterial culturing and culture broth are all conventional protocols in Molecular Biology, which were performed according to "Molecular Cloning A Laboratory Manual, $2^{nd}$ ed., Sambrook, J. et al. Science Press, 1993", so as to produce the expression vector pCVCG containing *Vitreoscilla* hemoglobin gene.
2) Identification of the Expression Vector pCVCG Containing *Vitreoscilla* Hemoglobin Gene
(1) PCR Identification The expression vector pCVCG (constructed in the invention) containing *Vitreoscilla* hemoglobin gene was identified by PCR amplification. The bacterial solution (2 μL) cultured in LB broth at 37° C. for 5 h was used as a template, and PCR amplification was carried out in a 25 μL, system. The primers were VCG-U1 (GCCGCAACCGATGACA, SEQ ID NO: 8) and VCG-D1 (GCCAAGTGGGCAGTTTACC, SEQ ID NO: 9). The target fragment was ~563 bp in length (FIG. 2). The above PCR amplification is a conventional PCR amplification preformed in a condition shown as follows: pre-denaturalizing at 94° C. for 5 min; amplifying for 35 cycles (94° C. for 30 sec, 58° C. for 30 sec, 72° C. for 30 sec); 72° C. for 5 min. The target fragment was ~563 bp in length (FIG. 2).
(2) Digestion and identification Plasmid pCVCG was extracted from the positive clones identified as above with the Plasmid Miniprep (~40 μg) kit (Axygen), and further identified to be pCVCG by digestion with a single enzyme HindIII (target fragment of 6627 bp) and by double enzymes XhoI+HindIII (target fragments of 1952 bp and 4675 bp) (FIG. 3).

Example 2

Figure 4:
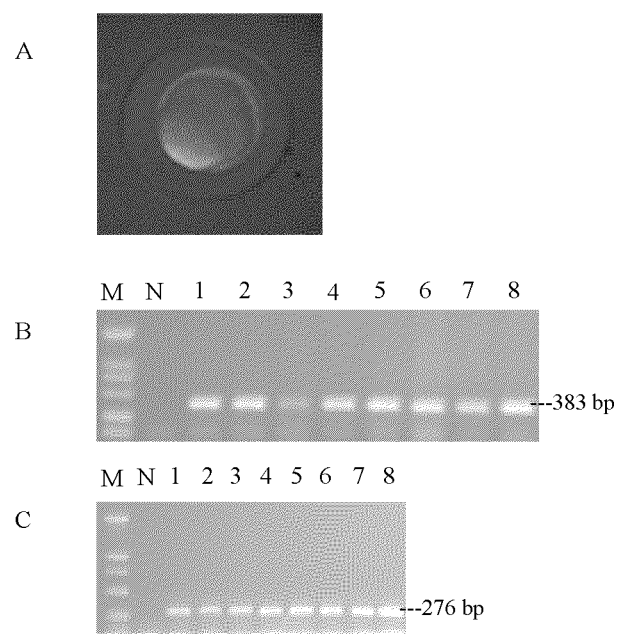
FIG. 4 shows the results of screening and testing of the vhb transgenic zebrafish, wherein A: GFP expression of the transgenic fish; B: integration of constructs of the transgenic fish in the transgenic fish genome detected by PCR; C: expression of the transgenic fish VHb gene detected by RT-PCR; N: GFP negative fish; 1-8, GFP positive fish in the transgenic fish families 1-8; M, DNA Marker DL2000.

The Use of a Recombinant Gene Enhancing the Ability of Fish to Tolerate Low do Stress in Modeling Organism Zebrafish (*Danio Rerio*), Comprising the Following Steps (1) Preparation of Transgenic Zebrafish Zebrafish AB strain was used. The plasmid DNA was extracted from the expression vector pCVCG containing *Vitreoscilla* hemoglobin gene and dissolved in ST solution (88 mmol/l NaCl, 10 mmol/l Tris-HCl, pH 7.5) to a final concentration of 85 ng/μl. Then the DNA solution was microinjected (Zhu Z, Li G, He L, et al. Novel gene transfer into the fertilized eggs of goldfish (*Carassius auratus* L. 1758). Z angew Ichthyol, 1985, 1:31-34) into the animal poles of zebrafish zygotes before the first cleavage. The DNA injection dose was 1-2 nl/zygote. The resultant zygotes were incubated and bred in 28.5° C. water.
(2) Breeding and Screening of the Transgenic Zebrafish Family which Stably Inheriting and Expressing the VHb Gene After vector pCVCG was introduced into zebrafish zygotes by micromanipulation, the zebrafish zygotes were screened for the embryos ($P_0$) expressing green fluorescence under a fluorescent microscope, as shown in FIG. 4A. These embryos ($P_0$) were then bred in circulating water till sexual maturity, and crossed with wildtype zebrafish. The embryos ($F_1$) globally expressing GFP were screened out and continually bred till sexual maturity, so as to obtain different transgenic fish families. Zebrafish were bred and propagated according to conventional protocols (Westerfield, 1993, The Zebrafish Book: A Guide for the Laboratory Use of Zebrafish (*Brachydanio rerio*). University of Oregon Press, Eugene, Oreg.).

DNA was extracted by the conventional phenol/chloroform method from about 0.1-0.2 cm² tail fin tissue of the transgenic zebrafish $F_1$ in the above different families. The conventional phenol/chloroform method was performed as follows: 0.4 ml DNA extraction solution (10 mmol/L EDTA, 10 mmol/L Tris.HCl, 300 mmol/L NaCl, 2% (weight/volume, g/L) SDS) was added into a 1.5 ml tube; after incubated in a 55° C. water bath for 1-2 h, the tissue was digested in a 37° C. water bath overnight; the digested tissue was then extracted with phenol, phenol/chloroform and chloroform, respectively; 2.5 volumes of ethanol was added, and the formed precipitate was transferred to another centrifuge tube immediately; the precipitate was washed once with 70% (volume ratio) ethanol and centrifuged at high speed for 1 min; the pellet was kept in a 37° C. incubator for 15 min after ethanol was completely poured out; the DNA pellet was dissolved in a proper volume of TE containing RNase (20 mg RNase/ml). The integration of pCVCG in the transgenic fish was confirmed by PCR technique, wherein the forward detecting primer (5'-ATCTGCCTGTAACCCATTCT-3', SEQ ID NO: 10) was located on carp β-actin promoter, reverse detecting primer (5'-AATACTTCTTTAATCGCACCC-3', SEQ ID NO: 11) was located on the target gene, i.e., *Vitreoscilla* hemoglobin gene, and PCR condition was shown as follows: pre-denaturalizing at 94° C. for 5 min; amplifying for 35 cycles (94° C., 30 s; 58° C., 30 s; 72° C., 30 s); finally extending at 72° C. for 5 min. The target fragment was 383 bp in length, as shown in FIG. 4B, which further confirmed the integration of pCVCG into zebrafish genome. It was found that the construct integration of carp β-actin promoter-driven VHb gene exists in the genome of all GFP-positive individuals, but not in the genome of any GFP-negative individuals (FIG. 4B).

Total RNA was extracted from GFP-positive $F_1$ fry of different zebrafish families and from the control sister fish group (TRIzol method). The extraction process was detailed as follows: (1) One zebrafish fry was homogenized thoroughly in 1 ml Trizol (Invitrogen) with an electro-homogenizer. (2) ⅕ volume of chloroform was added and the mixture was mixed thoroughly by inversing the container upside down for ~1 min. The mixture was kept at room temperature (20-25° C., same as below) for 5 min followed by centrifuging at 4° C., 12,000 rpm for 15 min. (4) The supernatant was carefully sucked out without touching the intermediate layer and transferred into a fresh 1.5 ml centrifuge tube. Same volume of isopropanol was added to and mixed with the supernatant by inversing the tube upside down gently, and then kept at room temperature for 5 min. (5) The mixture was centrifuged at 4° C., 12000 rpm for 10 min. (6) The supernatant was removed, and ⅔ volume of 70% (% volume) ethanol was added to the remained pellet. Then centrifugalization was carried out at 4° C., 12000 rpm for another 15 min to wash the pellet. (7) After removing the supernatant, the pellet was naturally dried out at room temperature, and then dissolved in a suitable amount of RNase-free water by pipetting up and down. (8) 1-2 μL of the resultant RNA solution was diluted to 100 uL. The diluent was detected by a spectrophotometer (Beckman DU-70) for $OD_{260}$, $OD_{280}$ and RNA concentration. The RNA sample was stored at −80° C. until later use. After that, cDNA was synthesized from 1 ug total RNA by Random 9 mers reverse transcription using the ReverTra Ace kit (TOYOBO) (the reaction system comprises 1 ug total RNA, Random primer, 2 ul 5× Buffer, 1 ul 10 mM dNTPs, 0.5 ul ReverTra Ace (100 U/ul), 10 U RNase Inhibitor, and DEPC water to make a total volume of 10 ul). The cDNA sample was diluted by 1:4 before PCR, and then 1-2 ul of the diluent was subjected to RT-PCR. The primers for detecting VHb gene expression were (5'-CGTTACCATTACCACGACTTT-3', SEQ ID NO: 12) and (5'-GCATCGCCCAATACTTCTT-3', SEQ ID NO: 13), and the target fragment was 276 bp in length. It was confirmed by RT-PCR that VHb mRNA was highly efficiently expressed in zebrafish. It was also found that VHb mRNA was expressed in GFP-positive individuals but not in GFP-negative individuals (FIG. 4C).

After confirmed by PCR, the transgenic zebrafish $F_1$ of different families were crossed with wildtype zebrafish. The offspring were screened by the green fluorescence tag for the positive fish, i.e., the transgenic zebrafish $F_2$. The embryos of $F_2$ were bred till sexual maturity and then crossed with wildtype fish, so as to reproduce offspring $F_3$. Then transgenic zebrafish family that stably inheriting and expressing VHb gene was obtained by PCR and RT-PCR confirmation.

(3) Screening of the VHb Transgenic Zebrafish Tolerating Low DO Stress

Male fish of the transgenic zebrafish family that stably expressing VHb gene were crossed with wildtype female zebrafish. After 24 h fertilization, the offspring embryos were divided into two groups, i.e., GFP-positive and GFP-negative embryos under a fluorescent microscope. The two groups of zebrafish were bred separately under the same condition according to standard protocols, among which the embryos without GFP expression were used as control fish. Seven-day transgenic fish and control fish, 100 each, were placed into an incubator (3131/Thermo; Form a Scientific, Inc., Marietta, Ohio) simultaneously and co-exposed to a condition of 2.5% $O_2$ (volume ratio), 97.5% (volume ratio) $N_2$ and 28.5° C. (0.91 mg/L, dissolved oxygen concentration in water). Additionally, another 40 transgenic fish and 40 control fish were routinely bred in a condition of normal oxygen concentration (7.6 mg/L). During the experiment, the fish were observed every 12 hours, and at the same time the death was recorded and the dead fish were removed.

Figure 5:
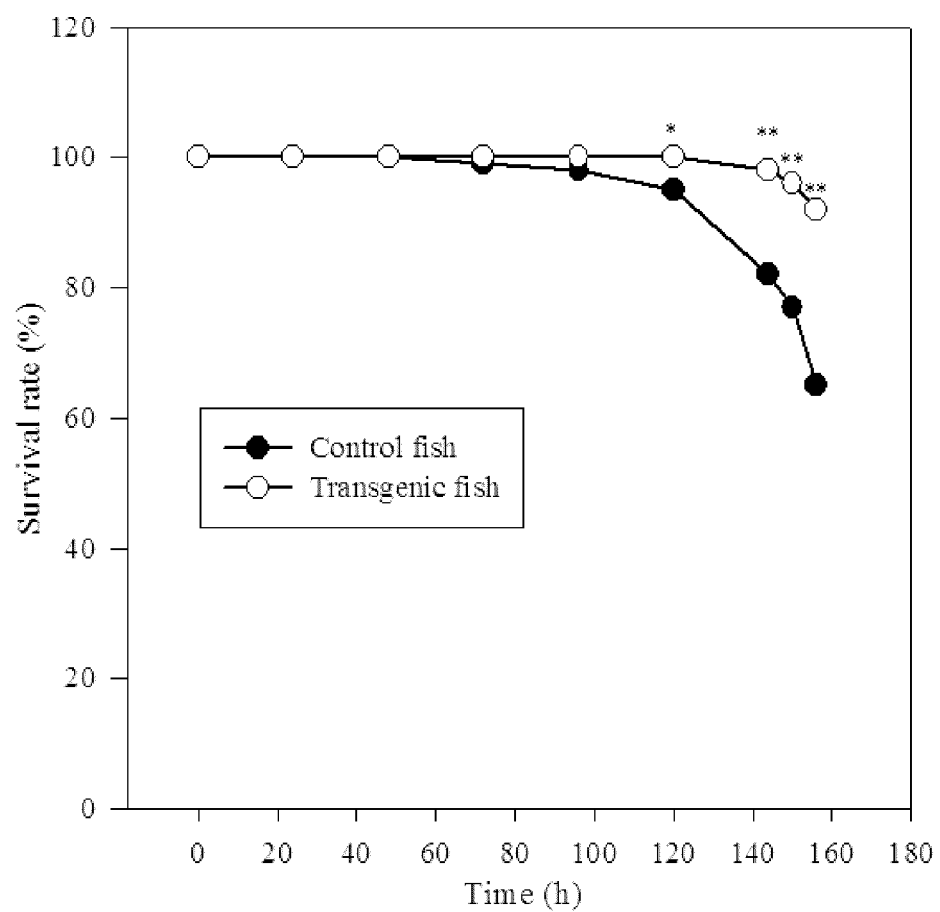
FIG. 5 shows the comparison of the survival rates between vhb transgenic fish and the control sister fish group in a low oxygen (2.5% $O_2$) condition, wherein chi square test is used to compare the survival rates, * represents the significant statistical difference (P<0.05), ** represents the extreme statistical significance (P<0.01).

It was found from the low DO stress test that the vhb transgenic zebrafish and the control fish both had a survival rate of 100% within 156 h in the normal DO condition (7.6 mg/L, dissolved oxygen concentration in water). However after 156 h low oxygen stress under a condition of 2.5% (volume ratio) $O_2$ (0.91 mg/l, dissolved oxygen concentration in water), the vhb transgenic zebrafish had a survival rate of 92% which was significantly higher than the survival rate of 65% of the control fish (FIG. 5). Consequently, the vhb transgenic zebrafish family with the tolerance to low DO stress was screened out.

Example 3

The Use of a Recombinant Gene Enhancing the Ability of Fish to Tolerate Low do Stress to Genetically Improve an Economically Farmed Species, Comprising the Following Steps (1) Preparation of Transgenic Blunt Snout Bream and Common Carp The important economically farmed species in China, i.e., blunt snout bream and common carp were used for preparing vhb transgenic fish. The plasmid DNA was extracted from the expression vector pCVCG containing *Vitreoscilla* hemoglobin gene using the Plasmid Miniprep kit (Axygen) and dissolved in ST solution (88 mmol/l NaCl, 10 mmol/l Tris-HCl, pH 7.5) to a final concentration of 85 ng/μl. Then the DNA extraction solution was microinjected (Zhu Z, Li G, He L, et al. Novel gene transfer into the fertilized eggs of goldfish (*Carassius auratus* L. 1758). Z angew Ichthyol, 1985, 1:31-34) into the animal poles of zygotes of blunt snout bream (common carp) before the first cleavage. The DNA injection dose was 1-2 nl/zygote. The resultant zygotes were incubated and bred according to the conventional methods.

(2) Screening of the Transgenic Fish with the Hypoxia Tolerance

After vector pCVCG was introduced into zygotes of blunt snout bream (common carp) by micromanipulation, the zygotes were screened for the embryos expressing green fluorescence under a fluorescent microscope (as shown in FIG. 4A). Fry were hatched from the screened embryos and bred in a pound. Two months later, DNA was extracted from about 0.1-0.2 $cm^2$ tail fin tissue of the transgenic fish according to the conventional phenol/chloroform method, and detected for the transgenosis. The conventional phenol/chloroform method was performed as follows: 0.4 ml DNA extraction solution (10 mmol/L EDTA, 10 mmol/L Tris.HCl, 300 mmol/L NaCl, 2% (weight/volume, g/L) SDS) was added into a 1.5 ml tube; after incubated in a 55° C. water bath for 1-2 h, the tissue was digested in a 37° C. water bath overnight; the digested tissue was then extracted with phenol, phenol/chloroform and chloroform, respectively; 2.5 volumes of ethanol was added, and the formed precipitate was transferred to another centrifuge tube immediately; the precipitate was washed once with 70% (volume ratio) ethanol and centrifuged at high speed for 1 min; the pellet was kept in a 37° C. incubator for 15 min after ethanol was completely poured out; the DNA pellet was dissolved in a suitable volume of TE containing RNase (20 mg RNase/ml). The integration of pCVCG in the transgenic fish was confirmed by PCR technique, wherein the forward detecting primer (5'-ATCTGC-CTGTAACCCATTCT-3', SEQ ID NO: 10) was located on carp β-actin promoter, reverse detecting primer (5'-AATACT-TCTTTAATCGCACCC-3', SEQ ID NO: 11) was located on the target gene, i.e., *Vitreoscilla* hemoglobin gene, and PCR condition was shown as follows: pre-denaturalizing at 94° C. for 5 min; amplifying for 35 cycles (94° C., 30 s; 58° C., 30 s; 72° C., 30 s); finally extending at 72° C. for 5 min. The target fragment was 383 bp in length (as shown in FIG. 4B), which further confirmed the integration of pCVCG into the transgenic fish genome.

Following observation under fluorescence and PCR detection, the obtained vhb transgenic blunt snout bream (common carp) $P_0$ and the control blunt snout bream (common carp) were bred separately in the pounds without any oxygenating equipment according to the conventional breeding process. After bred in such pounds for 1 year, the control blunt snout bream and control carp were dead because of hypoxia; whereas about 10% of the vhb transgenic blunt snout bream and vhb transgenic carps survived due to the hypoxia tolerance.

After further breeding till sexual maturity in the pounds, the survived vhb transgenic blunt snout bream and common carp were crossed with control fish. The transgenic fish ($F_1$) globally expressing GFP were screened out and continuously bred, so as to obtain the transgenic fish family with the hypoxia tolerance. Blunt snout bream and common carp were both bred and propagated according to conventional methods.

What is claimed is:

1. An isolated recombinant gene expression vector comprising the nucleotide sequence of SEQ ID NO: 5.

2. The isolated recombinant gene expression vector according to claim 1, wherein the expression vector is pCVCG.

3. A method for genetically improving the ability of a fish species to tolerate low dissolved oxygen stress comprising: microinjecting a transgene comprising a carp beta-actin gene promoter operatively linked to a recombinant *Vitreoscilla* hemoglobin gene into a zygote of said fish species; and selecting a transgenic fish species whose genome comprises the transgene and which exhibits an enhanced ability to tolerate low dissolved oxygen stress.

4. The method of claim 3, wherein the fish species is a farmed species.

5. The method according to claim 1, wherein said fish species is blunt snout bream.

6. Transgenic fish having an enhanced ability to tolerate low oxygen stress, wherein the genome of the transgenic fish comprises a transgene comprising a carp beta-actin gene promoter operatively linked to a recombinant *Vitreoscilla* hemoglobin gene, wherein expression of recombinant *Vitreoscilla* hemoglobin in the fish results in enhanced ability to tolerate low oxygen stress.

7. The transgenic fish according to claim 6, wherein said transgene comprises the nucleotide sequence of SEQ ID NO:5.

8. The transgenic fish according to claim 6, wherein said transgenic fish is an economically farmed species.

9. The transgenic fish according to claim 6, wherein said transgenic fish is a zebrafish, a blunt snout bream or a common carp.

* * * * *

SEQUENCE LISTING

```
<160> NUMBER OF SEQ ID NOS: 13

<210> SEQ ID NO 1
<211> LENGTH: 1213
<212> TYPE: DNA
<213> ORGANISM: Cyprinus carpio

<400> SEQUENCE: 1
cttttagacc ttcttacttt tggggattat ataagtattt tctcaataaa tatctcatat      60
cttactgtgg tttaactgct gaatctaaaa ttttaataca aaagtagtta tatttgttgt     120
acattgtaaa ctataactta acttcagttt cagagaaact catgtgctca aaatgtaaaa     180
aaagtttcct gttaaatatt ttgtaaatgt attgaagaca aaataagaaa aaaaaaatat     240
aagccactaa atcacactgt ccttggtatc agcaagagat tctgacataa tcagctgttt     300 ttgttttatta ctgccattga aggccatgtg cattagtccc aagttacaca ttaaaaagtc    360
acatgtagct taccaacatc agtgctgttc aagcacagcc tcatctacta ttcaaactgt     420
ggcaccatct aaaatatgcc agaatttttt tatttaatga atttgaccct gaaatatgta     480
ttaatatcac tcctgtgatt tttttgtaat cagcttacaa ttacaggaat gcaagcctga     540
ttcattacaa gtttcactac actttctctg acaacatcac ctactgaact cagaccagct     600
agttgctcct taagtataca atcatgtcac taatcctcat ttcaatgaaa ataccccta     660 ttgtacttgg tacttggtag ataaccacag agcagtatta tgccattatt gtgaatacaa     720
taagaggtaa atgacctaca gagctgctgc tgctgttgtg ttagattgta aacacagcac    780
aggatcaagg aggtgtccat cactatgacc aatactagca ctttgcacag gctctttgaa    840
aggctgaaaa gagccttatt ggcgttatca caacaaaata cgcaaatacg gaaaacaacg    900
tattgaactt cgcaaacaaa aaacagcgat tttgatgaaa atcgcttagg gatccccct     960 tgctcttcaa acaatccagc ttctccttct ttcactctca agttgcaaga agcaagtgta   1020
gcaatgtgca cgcgacagcc gggtgtgtga cgctggacca atcagagcgc agagctccga   1080
aagtttacct tttatggcta gagccgggca tctgccgtca tataaaagag cgcgcccagc   1140
gtctcagcct cactttgagc tcctccacac gcagctagtg cggaatatca tctgcctgta   1200
acccattctc taa                                                      1213

<210> SEQ ID NO 2
<211> LENGTH: 441
```

```
<212> TYPE: DNA
<213> ORGANISM: Vitreoscilla stercoraria

<400> SEQUENCE: 2
atgttagacc agcaaaccat taacatcatc aaagccactg ttcctgtatt gaaggagcat      60
ggcgttacca ttaccacgac tttttataaa aacttgtttg ccaaacaccc tgaagtacgt     120
cctttgtttg atatgggtcg ccaagaatct ttggagcagc ctaaggcttt ggcgatgacg     180
gtattggcgg cagcgcaaaa cattgaaaat ttgccagcta ttttgcctgc ggtcaaaaaa     240
attgcagtca acattgtca agcaggcgtg gcagcagcgc attatccgat tgtcggtcaa      300
gaattgttgg gtgcgattaa agaagtattg ggcgatgccg caaccgatga catttttggac   360 gcgtggggca aggcttatgg cgtgattgca gatgtgttta ttcaagtgga agcagatttg     420
tacgctcaag cggttgaata a                                               441

<210> SEQ ID NO 3
<211> LENGTH: 51
<212> TYPE: DNA
<213> ORGANISM: Simian virus 40

<400> SEQUENCE: 3
aataaagcaa tagcatcaca aatttcacaa ataaagcatt ttttttcactg c              51

<210> SEQ ID NO 4
<211> LENGTH: 1331
<212> TYPE: DNA
<213> ORGANISM: Cytomegalovirus

<400> SEQUENCE: 4
ttagttatta atagtaatca attacggggt cattagttca tagcccatat atggagttcc      60
gcgttacata acttacggta aatggcccgc ctggctgacc gcccaacgac ccccgcccat     120
tgacgtcaat aatgacgtat gttcccatag taacgccaat agggactttc cattgacgtc     180
aatgggtgga gtatttacgg taaactgccc acttggcagt acatcaagtg tatcatatgc     240
caagtacgcc ccctattgac gtcaatgacg gtaaatggcc cgcctggcat tatgcccagt     300
acatgacctt atgggacttt cctacttggc agtacatcta cgtattagtc atcgctatta     360
ccatggtgat gcggttttgg cagtacatca atgggcgtgg atagcggttt gactcacggg     420
gatttccaag tctccacccc attgacgtca atgggagttt gttttggcac caaaatcaac     480
gggactttcc aaaatgtcgt aacaactccg ccccattgac gcaaatgggc ggtaggcgtg     540
tacggtggga ggtctatata agcagagctg gtttagtgaa ccgtcagatc cggatccac      600 cggtcgccac catggtgagc aagggcgagg agctgttcac cggggtggtg cccatcctgg     660
tcgagctgga cggcgacgta aacggccaca agttcagcgt gtccggcgag ggcgagggcg     720
atgccaccta cggcaagctg accctgaagt tcatctgcac caccggcaag ctgcccgtgc     780
cctggcccac cctcgtgacc accctgacct acggcgtgca gtgcttcagc cgctaccccg     840
accacatgaa gcagcacgac ttcttcaagt ccgccatgcc cgaaggctac gtccaggagc     900
gcaccatctt cttcaaggac gacggcaact acaagacccg cgccgaggtg aagttcgagg     960
gcgacaccct ggtgaaccgc atcgagctga agggcatcga cttcaaggag gacggcaaca    1020
tcctggggca caagctggag tacaactaca acagccacaa cgtctatatc atggccgaca    1080
agcagaagaa cggcatcaag gtgaacttca agatccgcca caacatcgag gacggcagcg    1140
tgcagctcgc cgaccactac cagcagaaca cccccatcgg cgacggcccc gtgctgctgc    1200
ccgacaacca ctacctgagc acccagtccg ccctgagcaa agaccccaac gagaagcgcg    1260
```

```
atcacatggt cctgctggag ttcgtgaccg ccgccgggat cactctcggc atggacgagc   1320
tgtacaagta a                                                       1331

<210> SEQ ID NO 5
<211> LENGTH: 6627
<212> TYPE: DNA
<213> ORGANISM: Artificial sequence
<220> FEATURE:
<223> OTHER INFORMATION: Artificially synthesized

<400> SEQUENCE: 5
tagttattac tagcgctacc ggactcagat ctcgagcttt tagaccttct tactttgggg    60
gattatataa gtattttctc aataaatatc tcatatctta ctgtggttta actgctgaat   120
ctaaaatttt aatacaaaag tagttatatt tgttgtacat tgtaaactat aacttaactt   180
cagtttcaga gaaactcatg tgctcaaaat gtaaaaaaag tttcctgtta aatattttgt   240
aaatgtattg aagacaaaat aagaaaaaaa aatataagc cactaaatca cactgtcctt    300
ggtatcagca agagattctg acataatcag ctgtttttgt ttattactgc cattgaaggc   360
catgtgcatt agtcccaagt tacacattaa aaagtcacat gtagcttacc aacatcagtg   420
ctgttcaagc acagcctcat ctactattca aactgtggca ccatctaaaa tatgccagaa   480
tttttttatt taatgaattt gaccctgaaa tatgtattaa tatcactcct gtgatttttt   540
tgtaatcagc ttacaattac aggaatgcaa gcctgattca ttacaagttt cactacactt   600
tctctgacaa catcacctac tgaactcaga ccagctagtt gctccttaag tatacaatca   660
tgtcactaat cctcatttca atgaaaaata cccctattgt acttggtact tggtagataa   720
ccacagagca gtattatgcc attattgtga atacaataag aggtaaatga cctacagagc   780
tgctgctgct gttgtgttag attgtaaaca cagcacagga tcaaggaggt gtccatcact   840
atgaccaata ctagcacttt gcacaggctc tttgaaaggc tgaaaagagc cttattggcg   900
ttatcacaac aaaatacgca aatacggaaa acaacgtatt gaacttcgca acaaaaaaac   960
agcgattttg atgaaaatcg cttagggatc cccccttgct cttcaaacaa tccagcttct  1020
ccttctttca ctctcaagtt gcaagaagca agtgtagcaa tgtgcacgcg acagccgggt  1080
gtgtgacgct ggaccaatca gagcgcagag ctccgaaagt ttacctttta tggctagagc  1140
cgggcatctg ccgtcatata aaagagcgcg cccagcgtct cagcctcact ttgagctcct  1200
ccacacgcag ctagtgcgga atatcatctg cctgtaaccc attctctaag tcgacggtac  1260
cgcgggcccg ggcgccacca tgttagacca gcaaaccatt aacatcatca agccactgt   1320 tcctgtattg aaggagcatg gcgttaccat taccacgact tttataaaaa acttgtttgc  1380
caaacaccct gaagtacgtc ctttgtttga tatgggtcgc caagaatctt tggagcagcc  1440
taaggctttg gcgatgacgg tattggcggc agcgcaaaac attgaaaatt tgccagctat  1500
tttgcctgcg gtcaaaaaaa ttgcagtcaa acattgtcaa gcaggcgtgg cagcagcgca  1560
ttatccgatt gtcggtcaag aattgttggg tgcgattaaa gaagtattgg gcgatgccgc  1620
aaccgatgac attttggacg cgtggggcaa ggcttatggc gtgattgcag atgtgtttat  1680
tcaagtggaa gcagatttgt acgctcaagc ggttgaataa aggcggccgc gactctagat  1740
cataatcagc cataccacat tgtagaggt tttacttgct ttaaaaaacc tcccacacct  1800 cccccctgaac ctgaaacata aaatgaatgc aattgttgtt gttaacttgt ttattgcagc  1860
ttataatggt tacaaataaa gcaatagcat cacaaatttc acaaataaag catttttttc  1920
actgcattct agttgtggtt tgtccaagct tccgccatgc attagttatt aatagtaatc  1980
```

```
aattacgggg tcattagttc atagcccata tatggagttc cgcgttacat aacttacggt    2040
aaatggcccg cctggctgac cgcccaacga cccccgccca ttgacgtcaa taatgacgta    2100
tgttcccata gtaacgccaa tagggacttt ccattgacgt caatgggtgg agtatttacg    2160
gtaaactgcc cacttggcag tacatcaagt gtatcatatg ccaagtacgc ccctattga    2220 cgtcaatgac ggtaaatggc ccgcctggca ttatgcccag tacatgacct tatgggactt    2280
tcctacttgg cagtacatct acgtattagt catcgctatt accatggtga tgcggttttg    2340
gcagtacatc aatgggcgtg gatagcggtt tgactcacgg ggatttccaa gtctccaccc    2400
cattgacgtc aatgggagtt tgttttggca ccaaaatcaa cgggactttc caaaatgtcg    2460
taacaactcc gccccattga cgcaaatggg cggtaggcgt gtacggtggg aggtctatat    2520
aagcagagct ggtttagtga accgtcagat ccgggatcca ccggtcgcca ccatggtgag    2580
caagggcgag gagctgttca ccggggtggt gcccatcctg gtcgagctgg acggcgacgt    2640
aaacggccac aagttcagcg tgtccggcga gggcgagggc gatgccacct acggcaagct    2700
gaccctgaag ttcatctgca ccaccggcaa gctgcccgtg ccctggccca ccctcgtgac    2760
caccctgacc tacggcgtgc agtgcttcag ccgctacccc gaccacatga agcagcacga    2820
cttcttcaag tccgccatgc ccgaaggcta cgtccaggag cgcaccatct tcttcaagga    2880
cgacggcaac tacaagaccc gcgccgaggt gaagttcgag ggcgacaccc tggtgaaccg    2940
catcgagctg aagggcatcg acttcaagga ggacggcaac atcctggggc acaagctgga    3000
gtacaactac aacagccaca acgtctatat catggccgac aagcagaaga acggcatcaa    3060
ggtgaacttc aagatccgcc acaacatcga ggacggcagc gtgcagctcg ccgaccacta    3120
ccagcagaac acccccatcg cgacggcccc cgtgctgctg cccgacaacc actacctgag    3180
cacccagtcc gccctgagca agacccccaa cgagaagcgc gatcacatgg tcctgctgga    3240
gttcgtgacc gccgccggga tcactctcgg catggacgag ctgtacaagt aaagcggccg    3300
cgactctaga tcataatcag ccataccaca tttgtagagg ttttacttgc tttaaaaaac    3360
ctcccacacc tccccctgaa cctgaaacat aaaatgaatg caattgttgt tgttaacttg    3420
tttattgcag cttataatgg ttacaaataa agcaatagca tcacaaattt cacaaataaa    3480 gcatttttt cactgcattc tagttgtggt ttgtccaaac tcatcaatgt atcttaaggc    3540
gtaaattgta agcgttaata ttttgttaaa attcgcgtta aattttgtt aaatcagctc    3600 attttttaac caataggccg aaatcggcaa aatcccttat aaatcaaaag aatagaccga    3660
gatagggttg agtgttgttc cagtttggaa caagagtcca ctattaaaga acgtggactc    3720
caacgtcaaa gggcgaaaaa ccgtctatca gggcgatggc ccactacgtg aaccatcacc    3780
ctaatcaagt tttttggggt cgaggtgccg taaagcacta aatcggaacc ctaaagggag    3840
cccccgattt agagcttgac ggggaaagcc ggcgaacgtg gcgagaaagg aagggaagaa    3900
agcgaaagga gcgggcgcta gggcgctggc aagtgtagcg gtcacgctgc gcgtaaccac    3960
cacacccgcc gcgcttaatg cgccgctaca gggcgcgtca ggtggcactt tcggggaaa    4020 tgtgcgcgga accctatttg tttatttttc taaatacatt caaatatgt atccgctcat    4080 gagacaataa ccctgataaa tgcttcaata atattgaaaa aggaagagtc ctgaggcgga    4140
aagaaccagc tgtggaatgt gtgtcagtta gggtgtggaa agtccccagg ctccccagca    4200
ggcagaagta tgcaaagcat gcatctcaat tagtcagcaa ccaggtgtgg aaagtcccca    4260
ggctccccag caggcagaag tatgcaaagc atgcatctca attagtcagc aaccatagtc    4320
ccgcccctaa ctccgcccat cccgccccta actccgccca gttccgccca ttctccgccc    4380
```

-continued

```
catggctgac taatttttt tatttatgca gaggccgagg ccgcctcggc ctctgagcta    4440
ttccagaagt agtgaggagg ctttttgga ggcctaggct tttgcaaaga tcgatcaaga     4500
gacaggatga ggatcgtttc gcatgattga acaagatgga ttgcacgcag gttctccggc   4560
cgcttgggtg gagaggctat tcggctatga ctgggcacaa cagacaatcg gctgctctga   4620
tgccgccgtg ttccggctgt cagcgcaggg gcgcccggtt cttttgtca agaccgacct    4680
gtccggtgcc ctgaatgaac tgcaagacga ggcagcgcgg ctatcgtggc tggccacgac   4740
gggcgttcct tgcgcagctg tgctcgacgt tgtcactgaa gcgggaaggg actggctgct   4800
attgggcgaa gtgccggggc aggatctcct gtcatctcac cttgctcctg ccgagaaagt   4860
atccatcatg gctgatgcaa tgcggcggct gcatacgctt gatccggcta cctgcccatt   4920
cgaccaccaa gcgaaacatc gcatcgagcg agcacgtact cggatggaag ccggtcttgt   4980
cgatcaggat gatctggacg aagagcatca ggggctcgcg ccagccgaac tgttcgccag   5040
gctcaaggcg agcatgcccg acggcgagga tctcgtcgtg acccatggcg atgcctgctt   5100
gccgaatatc atggtggaaa atggccgctt ttctggattc atcgactgtg gccggctggg   5160
tgtggcggac cgctatcagg acatagcgtt ggctacccgt gatattgctg aagagcttgg   5220
cggcgaatgg gctgaccgct tcctcgtgct ttacggtatc gccgctcccg attcgcagcg   5280
catcgccttc tatcgccttc ttgacgagtt cttctgagcg ggactctggg gttcgaaatg   5340
accgaccaag cgacgcccaa cctgccatca cgagatttcg attccaccgc cgccttctat   5400
gaaaggttgg gcttcggaat cgttttccgg gacgccggct ggatgatcct ccagcgcggg   5460
gatctcatgc tggagttctt cgcccaccct agggggaggc taactgaaac acggaaggag   5520
acaataccgg aaggaacccg cgctatgacg gcaataaaaa gacagaataa aacgcacggt   5580
gttgggtcgt ttgttcataa acgcggggtt cggtcccagg gctggcactc tgtcgatacc   5640
ccaccgagac cccattgggg ccaataccgcc gcgtttctt ccttttcccc accccacccc   5700
ccaagttcgg gtgaaggccc agggctcgca gccaacgtcg gggcggcagg ccctgccata   5760
gcctcaggtt actcatatat actttagatt gatttaaaac ttcattttta atttaaaagg   5820
atctaggtga agatccttt tgataatctc atgaccaaaa tcccttaacg tgagttttcg    5880
ttccactgag cgtcagaccc cgtagaaaag atcaaaggat cttcttgaga tccttttttt   5940
ctgcgcgtaa tctgctgctt gcaaacaaaa aaaccaccgc taccagcggt ggtttgtttg   6000
ccggatcaag agctaccaac tcttttccg aaggtaactg gcttcagcag agcgcagata    6060
ccaaatactg tccttctagt gtagccgtag ttaggccacc acttcaagaa ctctgtagca   6120
ccgcctacat acctcgctct gctaatcctg ttaccagtgg ctgctgccag tggcgataag   6180
tcgtgtctta ccgggttgga ctcaagacga tagttaccgg ataaggcgca gcggtcgggc   6240
tgaacggggg gttcgtgcac acagcccagc ttggagcgaa cgacctacac cgaactgaga   6300
tacctacagc gtgagctatg agaaagcgcc acgcttcccg aagggagaaa ggcggacagg   6360
tatccggtaa gcggcagggt cggaacagga gagcgcacga gggagcttcc agggggaaac   6420
gcctggtatc tttatagtcc tgtcgggttt cgccacctct gacttgagcg tcgatttttg   6480
tgatgctcgt caggggggcg gagcctatgg aaaaacgcca gcaacgcggc ctttttacgg   6540
ttcctggcct tttgctggcc ttttgctcac atgttctttc ctgcgttatc ccctgattct   6600
gtggataacc gtattaccgc catgcat                                       6627
```

<210> SEQ ID NO 6
<211> LENGTH: 19

```
<212> TYPE: DNA
<213> ORGANISM: Artificial Sequence
<220> FEATURE:
<223> OTHER INFORMATION: oligonucleotide primer

<400> SEQUENCE: 6
ccatggtaga ccagcaacc                                                  19

<210> SEQ ID NO 7
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 7
gggtaacctt tattcaaccg                                                 20

<210> SEQ ID NO 8
<211> LENGTH: 16
<212> TYPE: DNA
<213> ORGANISM: Artificial Sequence
<220> FEATURE:
<223> OTHER INFORMATION: oligonucleotide primer

<400> SEQUENCE: 8
gccgcaaccg atgaca                                                     16

<210> SEQ ID NO 9
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 9
gccaagtggg cagtttacc                                                  19

<210> SEQ ID NO 10
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 10
atctgcctgt aacccattct                                                 20

<210> SEQ ID NO 11
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 11
aatacttctt taatcgcacc c                                               21

<210> SEQ ID NO 12
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 12
cgttaccatt accacgactt t                                               21
```

```
<210> SEQ ID NO 13
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 13
gcatcgccca atacttctt                                              19
```